(12) United States Patent
Xia et al.

(10) Patent No.: US 7,569,675 B2
(45) Date of Patent: *Aug. 4, 2009

(54) HIGH AFFINITY MONOCLONAL ANTIBODY FOR RECOGNIZING THE PROGESTERONE RECEPTOR (PR) AND METHOD FOR CREATING THE ANTIBODY

(75) Inventors: Haiying Xia, Union City, CA (US); Zhida Huang, Fremont, CA (US)

(73) Assignee: Spring Bioscience Corporation, Fremont, CA (US)

( * ) Notice: Subject to any disclaimer, the term of this patent is extended or adjusted under 35 U.S.C. 154(b) by 1018 days.

This patent is subject to a terminal disclaimer.

(21) Appl. No.: 10/242,092

(22) Filed: Sep. 11, 2002

(65) Prior Publication Data

US 2004/0141965 A1 Jul. 22, 2004

(51) Int. Cl.
- C07K 16/28 (2006.01)
- C12P 21/08 (2006.01)
- G01N 33/53 (2006.01)
- G01N 33/531 (2006.01)
- G01N 33/554 (2006.01)
- G01N 33/567 (2006.01)
- G01N 33/577 (2006.01)
- C12N 5/12 (2006.01)
- G01N 33/574 (2006.01)

(52) U.S. Cl. ............... 530/388.22; 435/7.23; 435/7.95; 435/40.52; 435/70.21; 435/449; 435/334; 435/960; 436/503; 436/518; 436/519; 436/548; 436/813

(58) Field of Classification Search ........... 435/7.23, 435/7.95, 40.52, 70.21, 449, 334, 346, 960; 436/503, 518, 519, 548, 164, 813; 530/388.22; 424/185.1, 198.1, 277.1
See application file for complete search history.

(56) References Cited

U.S. PATENT DOCUMENTS

| | | | | |
|---|---|---|---|---|
| 4,543,439 | A | | 9/1985 | Frackelton, Jr. et al. |
| 4,742,000 | A | * | 5/1988 | Greene ............ 435/7.21 |
| 4,859,595 | A | * | 8/1989 | Strosberg et al. ........ 435/6 |
| 5,283,190 | A | * | 2/1994 | Traish et al. .......... 435/334 |
| 5,675,063 | A | * | 10/1997 | Knight .............. 800/14 |
| 2003/0124130 | A1 | * | 7/2003 | Brown ............. 424/155.1 |

OTHER PUBLICATIONS

Misrahi et al., 1987. Complete amino acid sequence of the human progesterone receptor deduced from cloned cDNA. Biochemical and Biophysical Research Communications 143 (2): 740-748.*

Owens et al., 1994. The genetic engineering of monoclonal antibodies. J. Immunolog. Meth. 168: 149-165.*

Harlow et al., 1988. Antibodies. A Laboratory Manual. Cold Spring Harbor Laboratory, Cold Spring Harbor. pp. 72-77.*

Mote et al., 2001. Detection of progesterone receptor forms A and B by immunohistochemical analysis. J. Clin. Pathol. 54(8): 624-630.*

Soomro et al., 1990. Demonstration of progesterone receptors in paraffin wax sections of breast carcinoma. J. Clin. Pathol. 43: 671-674.*

Press et al., Jun. 2002. Comparison of different antibodies for detection of progesterone receptor in breast cancer. Steroids 67: 799-813.*

NCBI Blast 2 Sequences. Alignment of gi110611914, Human Progesterone Receptor, with gi130896, Rabbit Progesterone Receptor. Website www.ncbi.nlm.nih.gov/blast/bl2seq.*

NCBI Blast 2 Sequences. Alignment of gi110611914, Human Progesterone Receptor, with gi112363098, Mouse Progesterone Receptor. Website www.ncbi.nlm.nih.gov/blast/bl2seq.*

"New Monoclonal Antibodies To Oestrogen and Progesterone receptors Effective for Paraffin Section Immunohistochemistry", Debra J. Bevitt, et al., Journal of Pathology, vol. 183, pp. 228-232 (1997).

"Production of Stable Rabbit-Mouse Hybridomas That Secrete Rabbit mAb of Defined Specificity", T.J.G. Raybould and Miyoko Takahashi, Science, vol. 240, pp. 1788-1790 (1998).

"Immunohistochemical Assay For Oestrogen Receptors in Paraffin Wax Sections Of Breast Carcinoma Using A New Monoclonal Antibody", Aihua Huang, Norman M. Pettigrew, and Peter H. Watson, Journal of Pathology, vol. 180, pp. 223-227 (1996).

"Preparation And Properties Of Monoclonal And Polyclonal Antibodies To Mouse Epidermal Growth Factor (EGF) Receptors: Evidence For Cryptic EGF Receptors In Embryonal Carcinoma Cells" Ann Weller, Jennifer Meek, and Eileen D. Adamson, Development 100, 351-363 (1987).

(Continued)

Primary Examiner—Christopher L. Chin
Assistant Examiner—James L Grun
(74) Attorney, Agent, or Firm—Richard Aron Osman

(57) ABSTRACT

A lagomorph derived monoclonal antibody for recognizing the progesterone receptor (PR) (clone SP2) with immunohistochemistry and methods for creating such an antibody are disclosed. No need of target retrieval in immunohistochemistry is their prominent advantage compared to currently available PR antibody. Furthermore, the very low background when the lagomorph derived monoclonal antibody is used in immunohistochemistry is also impressive. The immunohistochemistry comparative study with about fifty clinical specimens showed that the new PR antibody (clone SP2) antibody had favorable results when compared to mouse monoclonal antibody PR (clone 1A6), the best one in the current market. The PR antibody may prove of great value in the assessment of PR status in human breast cancer. Humanized versions of the PR antibody may provide therapeutic benefits.

9 Claims, 2 Drawing Sheets

OTHER PUBLICATIONS

"Site-Directed Serology With Synthetic Peptides Representing The Large Glycoprotein G Of Respiratory Syncytial Virus", Erling Norrby, et. al., Proceeding of the National Academy of Science-Microbiology, vol. 84, pp. 6572-6576 (1987).

"Comparison of Cell Surface Human Melanoma-Associated Antigens Identified by Rabbit and Murine Antibodies", Jean-Claude Bystryn, Jack Steve Jacobsen, Philip Liu, and Joy Heaney-Kieras, Hybridoma, vol. 1, No. 4, pp. 465-472 (1982).

"Rabbit Monoclonal Antibodies: Generating a fusion Partner To Produce Rabbit-Rabbit Hybridomas", Helga Spieker-Polet, Perianna Sethupathi, Pi-Chen Yam, and Katherine L. Knight, Proceeding of the National Academy of Science-Immunology, vol. 92, pp. 9348-9352 (1995).

"An Expanded View Of The Ontogeny Of The Rabbit Humoral Immune System", M.A. Crane, C. Raman, and K.L. Knight, $52^{nd}$ Forum in Immunology, pp. 486-494, Res. Immunol. 144: 486-494, 1993.

"Polymorphism and Utilization of Human $V_H$ Genes", Eric C.B. Milner, Wendy O. Hufnagle, Annuska M. Glas, Ivy Suzuki, and Catherine Alexander, Annals New York Academy of Sciences, pp. 50-61, 764: 50-61, 1995.

* cited by examiner

HIGH AFFINITY MONOCLONAL ANTIBODY FOR RECOGNIZING THE PROGESTERONE RECEPTOR (PR) AND METHOD FOR CREATING THE ANTIBODY

FIELD OF THE INVENTION

The present invention relates to the field of antibodies. In particular the present invention discloses an antibody ideal for immunohistochemical staining without difficult target retrieval procedures.

BACKGROUND OF THE INVENTION

A standard technique for medical diagnosis is to take a biopsy (a tissue sample), and have that biopsy analyzed by a laboratory. For example, taking a biopsy and testing the biopsy is often used to detect cancer.

The testing of biopsies for estrogen and progesterone receptors (ER and PR) has proven very useful in the detection and treatment of breast cancer. Specifically, the assessment of estrogen and progesterone receptors (ER and PR) status in breast cancer is widely used for the prediction of response to endocrine therapy and as a prognostic marker.

The immunohistochemistry (IHC) method is considered as a specific, sensitive, and economical method for the determination of estrogen and progesterone receptors status. The currently available ER and PR antibodies used for immunohistochemistry testing on formalin-fixed, paraffin-embedded tissues are either mouse monoclonal/polyclonal antibodies or rabbit polyclonal antibodies. The current antibody that has proven to be the best is the clone 1D5 mouse monoclonal antibody for ER and clone 1A6 mouse monoclonal antibody for PR.

Unfortunately, all the current ER and PR antibodies used for immunohistochemistry testing require a heat pretreatment for accurate results. This heat pretreatment is required for target retrieval. The heat pretreatment is a difficult and time-consuming step. Furthermore, the heat pretreatment may produce some problems, such as increasing staining background and inconsistency of the results. Therefore, it would be very desirable to have other testing systems that do not require this troublesome heat pre-treatment step.

SUMMARY OF THE INVENTION

High affinity monoclonal antibodies for recognizing ER (clone SP1) and PR (clone SP2) with immunohistochemistry and methods for creating such antibodies are disclosed. To create the high affinity monoclonal antibodies, an appropriate antigen is first created. For the estrogen receptor (ER), an 18 mer peptide located in the C-terminal of human ER alpha protein (578-595 aa) was synthesized on a semi-automatic peptide synthesizer. Recombinant protein preparation was used to create the progesterone receptor (PR) antigen. Specifically, the PR gene encoding human PR B Form 412-562 aa was amplified by polymerase chain reaction (PCR) from human uterus PCR-Ready cDNA and then ligated into an expression plasmid.

Next, the created antigen is used to immunize a lagomorph host. The lagomorph has an immunogenic response to the created antigen. After being given enough time for a strong immune response, lymphocytes are harvested from the lagomorph spleen. Next, the lymphocytes are fused with a myeloma-like tumor (plasmacytoma) to create hybridoma colonies. Various hybridoma colonies are then characterized to select the desired antibody.

The lagomorph derived antibodies have demonstrated a very high affinity. With the lagomorph derived antibodies, there is no need for target retrieval when performing immunohistochemistry testing. Furthermore, the strong signal and very low background in immunohistochemistry testing has also been impressive. Thus, these antibodies will likely prove to have great value in the assessment of ER/PR status in human breast cancer. Furthermore, humanized versions of these antibodies may provide therapeutic benefits.

Other objects, features, and advantages of present invention will be apparent from the company drawings and from the following detailed description.

BRIEF DESCRIPTION OF THE DRAWINGS

The objects, features, and advantages of the present invention will be apparent to one skilled in the art, in view of the following detailed description in which.

DETAILED DESCRIPTION OF THE PREFERRED EMBODIMENT

Figure 1:
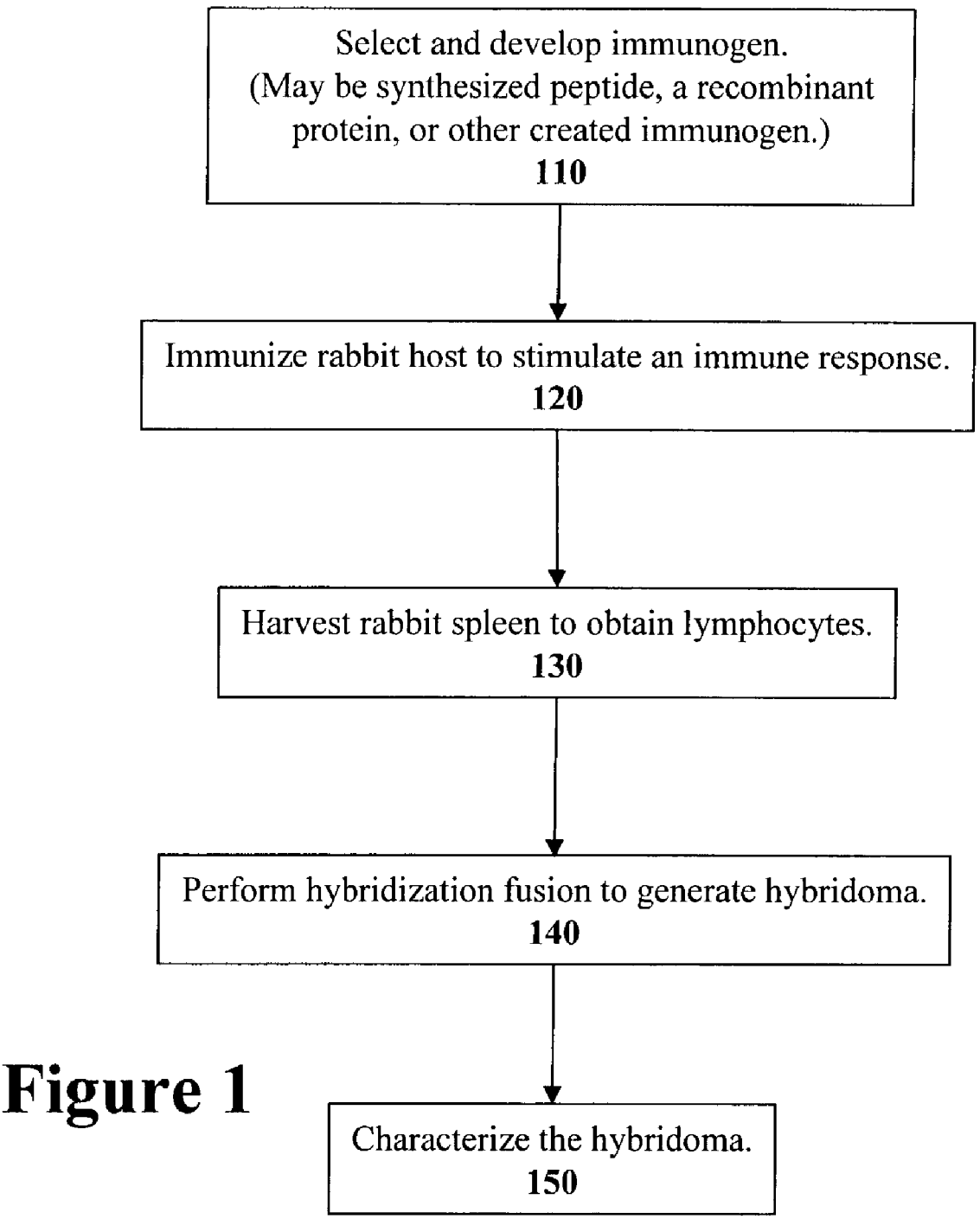
FIG. 1 illustrates the overall procedure used to create a high affinity monoclonal antibody using a rabbit host.

ER and PR rabbit monoclonal antibodies and a method for creating such monoclonal antibodies are disclosed. In the following description, for purposes of explanation, specific nomenclature is set forth to provide a thorough understanding of the present invention. However, it will be apparent to one skilled in the art that these specific details are not required in order to practice the present invention. For example, the present invention has been described with reference to the creation of antibodies for testing estrogen and progesterone receptor status. However, the same techniques can easily be applied to create other types of rabbit monoclonal antibodies for use in immunohistochemistry without heat pretreatment.

Overview

As set forth in the background, the ER clone 1D5 and PR clone 1A6 mouse monoclonal antibodies are currently the best available antibodies for immunohistochemistry testing for estrogen and progesterone receptors on formalin-fixed, paraffin-embedded tissue samples. However, the tissue samples must be prepared with a heat pretreatment that is time-consuming, difficult to automate, and potentially troublesome.

In general, it has been found that a rabbit monoclonal antibody has higher affinity than a mouse monoclonal antibody. Due to this higher affinity, it was hypothesized that rabbit monoclonal antibodies would be very effective for immunohistochemistry testing. Ideally, it would be very beneficial to create an antibody that does not require heat pretreatment of formalin-fixed, paraffin-embedded tissue before immunohistochemistry testing. Thus, an effort to generate rabbit monoclonal antibody to ER was pursued.

Before attempting to develop rabbit monoclonal antibodies, an examination of purified rabbit polyclonal antibodies from immunized rabbit serum was performed. These antibodies were found to be effective in immunohistochemistry after target retrieval. The same rabbits' spleen cells were then used to develop rabbit monoclonal antibodies.

Rabbits are one of the best sources of high affinity polyclonal antibodies. To generate monoclonal antibodies, the fusion of an antibody producing lymphocyte with a tumor cell is generally performed to create a hybridoma. (A Hybridoma is a hybrid cell produced by the fusion of an antibody-producing lymphocyte with a tumor cell and used to culture continuously a specific monoclonal antibody.) However, since myeloma-like tumors were unknown in the rabbit, it had been impossible to use hybridoma approach to generate a rabbit monoclonal antibody. In 1995, K. Knight and colleagues succeeded in producing a myeloma-like tumor (plasmacytoma) in transgenic rabbits expressing the v-abl and c-myc oncogenes (Spieker-Polet, Sethupathi et al. 1995). The teachings concerning the creation of an immortalized rabbit hybridoma fusion partner as set forth in U.S. Pat. No. 5,675,063 are hereby incorporated by reference.

With this rabbit plasmacytoma cell line (240E-1) available, various teams started to make rabbit monoclonal antibody with traditional hybridoma approach. A 240E derivative cell line (240E-w) that provided higher fusion efficiency and hybridoma stability was developed by UCSF and licensed by Epitomics.

The availability of rabbit monoclonal antibodies provides a number of different advantages. First, rabbit antisera are generally considered to have a higher affinity and recognize a greater variety of epitopes than antisera generated from mice. Thus, it was theorized that monoclonal antibodies generated from rabbits would also possess similar superior features compared to monoclonal antibodies from mice. Second, rabbit monoclonal antibodies are expected to recognize many antigens that are not immunogenic in mice, including mouse proteins (Krause 1970; Bystryn, Jacobsen et al. 1982; Norrby, Mufson et al. 1987; Weller, Meek et al. 1987; Raybould and Takahashi 1988). Third, because of the larger size of the rabbit spleen, a much larger pool of hybridomas can be generated from a single rabbit host. The much larger pool of hybridomas provides many more opportunities to select the desired monoclonal antibodies.

Rabbit Monoclonal Antibody Generation

FIG. 1 illustrates the overall procedure used to create a high affinity monoclonal antibody using a rabbit host. A description of the procedure will be provided with reference to the creation of rabbit monoclonal antibodies for estrogen and progesterone receptors. However, the overall procedure of FIG. 1 may be followed to develop other high affinity antibodies.

Antigen Development

Referring to step 110 of FIG. 1, the first step is to select and generate the antigens that will be used to create an immune response. Different techniques may be used to create different antigens. To create antibodies for immunohistochemistry testing for estrogen and progesterone receptors, peptide synthesis and recombinant protein preparation were used, respectively. However, other immunogen creation methods may also be used such as purified native proteins or live cells ER Antigen: Peptide Preparation To create an antigen for the estrogen receptor (ER), a peptide was synthesized. Specifically, an 18 mer peptide located in the C-terminal of human ER alpha protein (578-595 aa) was synthesized on a semi-automatic peptide synthesizer. The peptide was covalently conjugated to a carrier molecule. In one embodiment, a keyhole limpet haemocyanin (KLH) carrier molecule was used. The peptide was also conjugated to bovine serum albumin (BSA) for immunoassay.

PR Antigen: Recombinant Protein Preparation

Advantages of using recombinant protein as immunogen over peptide include multiple epitopes and possibly mimicking native structure of the protein. Thus, recombinant protein preparation was used to create the progesterone receptor (PR) antigen. Specifically, the PR gene encoding human PR B Form 412-562 aa was amplified by polymerase chain reaction (PCR) from human uterus PCR-Ready cDNA. The PR gene was then ligated into an expression plasmid. The presence of the PR gene in the plasmid was verified by DNA sequencing and the expressed PR 412-562 aa recombinant protein in E.Coli was confirmed by the protein size on the Commasie blue stained SDS-polyacrylamide gel and western blotting. The affinity purified recombinant protein was used as immunogen.

Host Immunization

Referring back to FIG. 1, after the creation of a desired immunogen at step 110, the next step of the procedure is to immunize a host with the created immunogen as set forth in step 120. In one embodiment of the present invention, New Zealand White rabbits were injected with the 0.2 mg ER peptide-KLH immunogen or the PR recombinant protein immunogen in complete Freund's adjuvant subcutaneously. Other lagomorphs could also be used.

After the initial immunization, the host animals were then boosted with the immunogen every twenty-one days for five more times in the same manner with incomplete Freund's adjuvant. Near the end of the immune response period, the rabbit serum was tested by immunoassay and immunohistochemical staining (IHC). The rabbit with the strongest titer in immunoassay and IHC was selected for a final boost, which was injected intravenously with the same antigen, but three times the regular amount four days before the sacrificing.

Referring again to FIG. 1, after sacrifice, the rabbit's spleen is harvested at step 130 to obtain the antibody producing lymphocytes. Due to the size of the rabbit spleen, a large pool of antibody producing lymphocytes is available from a single rabbit host.

Hybridization Fusion

To create a continuous antibody supply from a harvested lymphocyte, an immortalized hybridoma is created by fusing the lymphocyte with a fusion partner at step 140. One possible technique for creating such a rabbit hybridoma is disclosed in U.S. Pat. No. 5,675,063, which is hereby incorporated by reference in its entirety.

In one embodiment, the fusions were performed using conventional methodology wherein $1.5 \times 10^8$ to $3 \times 10^8$ lymphocytes from an immunized rabbit and the fusion partner (240E-w) were fused at a ratio of 2:1 with PEG 4000 (Sigma P7181) at 37° C. in serum-free medium. The cells were plated in 96-well cell culture plates at approximately $1 \times 10^5$ lymphocytes per well in medium with 15% Fetal Bovine Serum (FBS).

After 48 hours, hypoxanthanine aminopterin and thymidine (HAT) was added to the culture. The medium was changed every week. Hybridoma colonies usually were observed after 2 to 5 weeks.

Hybridoma Characterization

Finally, at step 150, the various hybridoma colonies are characterized using known testing methods. Specifically, supernatants from the hybridoma colonies were tested for the presence of antibody specific for the immunogen by Enzyme Linked Immunosorbent Assay (ELISA) and immunohistochemistry as a secondary screen assay. The hybridomas were subcloned by limited dilution. For feeder cells, one embodiment used the fusion partner 240E-w at $2\times10^4$ cells per well.

Enzyme Linked Immunosorbent Assay (ELISA)

The Enzyme Linked Immunosorbent Assay (ELISA) was performed in 96-well microtiter plates that were coated overnight with immunogen at 1 µg/ml. The plates were then saturated with 2% BSA, following by antibody supernatant incubation for 1 hour at room temperature. After washing with PBS-Tween, alkaline phosphatase conjugated goat anti-rabbit IgG (1:5,000; PIERCE 31340) were incubated for another hour, and plates were washed again, and developed in presence of substance P-NPP (PIERCE 34045). Color development was read at 405 nm in an ELISA plate.

Antibody Purification

Tissue culture supernatants containing rabbit monoclonal antibodies to ER and PR were incubated with immobilized rProtein A™ (IPA-400HC; RepliGen) on the column. The column was washed extensively with PBS to remove the nonspecific binding proteins until OD280 was less than 0.01. The rabbit IgGs were eluted with 0.2 M Citrate Acid pH 2.5. The eluents were dialyzed against PBS for overnight at 4° C.

Immunohistochemistry

To perform immunohistochemistry, 5 µm of formalin-fixed, paraffin-embedded tissue sections were mounted on slides coated with polylysine. Sections were deparaffinized, rehydrated, heat pretreatment (or no need pretreatment), treated with hydrogen peroxide block (0.3% H2O2+0.05% NaN3) for ten minutes at room temperature to block the endogenous peroxidase, then incubated with primary antibodies (clone SP1, 1D5, SP2, and 1A6) in protein blocking solution for ten minutes at room temperature, incubated with biotinylated goat anti-mouse and anti-rabbit secondary antibodies for ten minutes at room temperature, streptavidin-peroxidase for ten minutes at room temperature, and finally incubated with DAB chromogen for ten minutes at room temperature. Slides were counterstained by hematoxylin and were covered by aqueous mounting media.

Comparison Testing

To compare the new rabbit monoclonal antibodies, a comparison test was performed. No heat pretreatment of sample tissues was performed for tests using the new rabbit monoclonal antibodies (clone SP1 and SP2 at 2 µg/ml concentration). Heat pretreatment of sample tissues was performed for 1D5, 1A6 mouse monoclonal antibodies (at 2 µg/ml concentration). Heat pretreatment was performed by bringing 10 mM citrate buffer (pH 6.0) containing the tissue sections to a boil using microwave on high power and then continuing to boil at low power for an additional ten minutes. This heat pretreatment was followed by at least twenty minutes standing time before addition of primary antibody.

The standards using for the immunohistochemistry testing was as follows:

| Observation | Conclusion |
|---|---|
| 0-5% staining | negative |
| >5% staining | positive |

Two different observers scored the test slides. In each case, five representative fields (40× objective on Olympus microscope) within each section were selected for assessment. Brown staining of tumor cell nuclei was taken as positive. A tumor was considered "ER-positive" if average proportion of positive cells in five fields was greater than 5%, and negative if less than 5%.

Antibody Affinity Assay

ELISA was performed to determine antibody affinities. 96-well micro-titer plates were coated overnight with ER peptide conjugated to BSA, human ER alpha recombinant protein (1-300 aa), and human PR B Form recombinant protein (412-562 aa) at 1.0 µg/ml. The plates were saturated with 2% BSA, followed by antibody incubation with serial dilution (200 nM, 100 nM, 50 nM, 25 nM, 12.5 nM, 6.25 nM, 3.125 nM, 1.56 nM, 0.78 nM, 0.39 nM, and 0.2 nM). Clone SP1 was incubated with the wells coated with ER peptide conjugated to BSA and clone 1D5 was incubated with wells coated with ER alpha recombinant protein. Clone SP2 and 1A6 were incubated with wells coated with PR B Form recombinant protein 412-562 aa. Each sample was duplicated. After washing with PBS-Tween, HRP conjugated goat anti-rabbit and mouse IgGs were incubated. The plates were washed again, and were developed with TMB single solution for 15 minutes. The reaction was stopped by adding 0.5N $H_2SO_4$. OD was measured at 450 nm.

Rabbit Monoclonal Antibody Immunohistochemistry Testing

Figure 2:
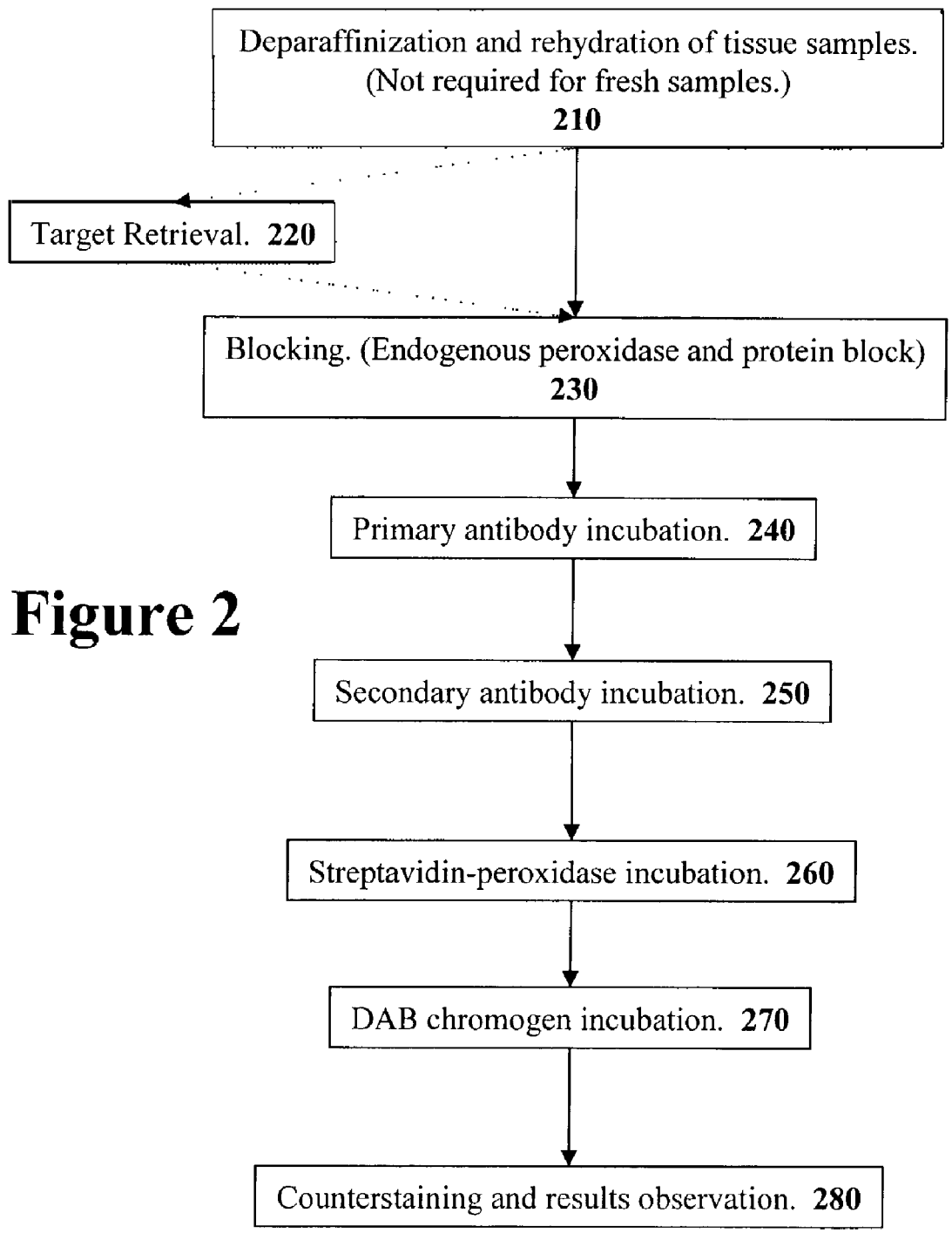
FIG. 2 illustrates a set of steps for performing immunohistochemistry without target retrieval with antibodies created from rabbit hybridomas.

The rabbit based monoclonal antibodies of the present invention have proven to be ideal for immunohistochemistry testing purposes. FIG. 2 illustrates how the rabbit based monoclonal antibodies of the present invention may be used in performing immunohistochemistry testing.

Referring to step 210 of FIG. 2, the first step is to prepare a formalin-fixed, paraffin-embedded (FFPE) tissue sections for testing. The tissue sections are deparaffinized and then rehydrated. Obviously, if the tissue samples are fresh, then this first step does not need to be performed.

Then, with the prior art antibodies, the tissue samples must be processed with a target retrieval step 220. One reason for this target retrieval may be needed is that formaldehyde in the FFPE tissue sections may react with amino acids within the epitope, such that the antibody will be unable to bind to the epitope. If there are such conformational changes resulting from the reaction of formaldehyde with amino acids adjacent to the epitope, these can often be reversed using proteolytic enzyme digestion or target retrieval. One common method of performing target retrieval is to perform a heat pretreatment of the deparaffinized and rehydrated tissue sample. However, the heat pretreatment process may cause a conformational change that destroys the desired epitopes, or alters them to reduce reactivity with the antibody. Thus, overheating of tissue sections during embedding, drying, or rehydration can induce detrimental effects on immunostaining. It is essential not to overheat at any stage of processing if immunostaining is to be optimally sensitive.

With the rabbit based monoclonal antibodies of the present invention, step 220 is not required. Thus, the second step with the rabbit based monoclonal antibodies is to perform the blocking of step 230. In blocking step 230, the tissue sample may be treated with hydrogen block (0.3% $H_2O_2$+0.05% $NaN_3$) for ten minutes at room temperature to block the endogenous peroxidase. However, this step is not necessary if alkaline phosphatase is used instead of peroxidase.

After the blocking step, the tissue sample is incubated with the primary monoclonal antibody at step 240. For the testing of estrogen receptors, the rabbit monoclonal antibody clone SP1 is used. For the testing of progesterone receptors, the rabbit monoclonal antibody clone SP2 is used. The incubation may be performed for ten minutes at room temperature.

After the primary antibody incubation, the tissue sample is then incubated with a secondary antibody at step 250. Specifically, an anti-rabbit secondary antibody is used. The anti-rabbit secondary antibody amplifies the signal since it binds to the primary antibody used in the previous step.

Next, at step 260, the tissue sample may be incubated with a streptavidin-peroxidase for ten minutes at room temperature. The streptavidin-peroxidase incubation further amplifies the signal by binding with the secondary antibody. Finally, the tissue sample may be incubated with a substrate chromogen for ten minutes at room temperature at step 270. A DAB chromogen or Enhanced DAB chromogen may be used in step 270.

For additional clarity, the user may perform counter-staining before observing the results at step 280. The counter-staining may be performed using hematoxylin.

ER and PR Rabbit Monoclonal Antibody Results

The previously set forth procedure worked well for creating ER and PR rabbit monoclonal antibodies. Ten 96-well plates fusion were successfully performed with partner cells (240E-w). After an ELISA screening, 36 positive clones were tested for tissue staining screen. Among the various clones, the two best clones (#26 and #39) were selected, which gave strong signal and very low background in tissue staining without heat pretreatment. These two clones were then subcloned in order to obtain monoclonal hybridomas. From clone #39, the monoclonal #59 gave the strongest staining, and was thus named as clone SP1. Likewise, 45 positive clones were tested for tissue staining screen. Among the various clones, the two best clones (#42 and #88) were selected, which gave strong signal and very low background in tissue staining without heat pretreatment. These two clones were then subcloned in order to obtain monoclonal hybridomas. From clone #88, the monoclonal #5 gave the strongest staining, and was thus named as clone SP2.

The antibodies were then tested using the immunohistochemistry procedures set forth in the previous section. Positive staining of nuclei was seen in both malignant and few normal epithelial cells in sections stained by the monoclonal ER antibodies in immunohistochemistry testing. It was negative in sample tissues that express no ER protein and positive in sample tissues that express ER protein.

Of the forty-seven cases tested, four cases showed prominent cytoplasmic staining with mouse antibody 1D5 (requiring heat pretreatment) but not with rabbit monoclonal antibody clone SP1. Twenty-six of the forty-seven cases examined were ER-positive (55.3%) and 21 negative (44.7%) with mouse antibody 1D5 after microwave heat pretreatment. Without any heat pretreatment, 55.3% (26/47) of the forty-seven cases were positive with new rabbit monoclonal antibody SP1. The staining results were almost same as that of mouse antibody 1D5. However, three cases that were only weakly stained with mouse antibody 1D5, were obviously stronger with the new rabbit monoclonal antibody SP1. Most of staining signals with new rabbit monoclonal antibody SP1 (with no heat pretreatment) were the same as or stronger than that of mouse antibody 1D5 (with heat pretreatment), but three cases were weaker (but still in positive range) than that of mouse antibody 1D5. Note that none of the forty-seven cases examined was positive with 1D5 without microwave heat pretreatment.

Positive staining of nuclei was seen in both malignant and few normal epithelial cells in sections stained by the monoclonal PR antibodies in immunohistochemistry testing. It was negative in sample tissues that express no PR protein and positive in sample tissues that express PR protein.

Nineteen of the forty-three cases examined were PR-positive (44.2%) and twenty-four negative (55.8%) with clone 1A6 after microwave heat pretreatment. Without heat pretreatment, 44.2% (19/43) was positive with the new rabbit monoclonal antibody SP1. None of the forty-three cases examined was positive with 1A6 without microwave heat pretreatment.

Antibody affinity assay shows that clone SP1 gave OD450 reading of 1.0 at 3.125 nM, while clone 1D5 gave OD450 reading of 1.0 at 25 nM. Thus, the affinity of clone SP1 is about eight times higher than clone 1D5. Clone SP2 gave OD450 reading of 1.0 at 3.125 nM, while clone 1A6 gave OD450 reading of 1.0 at 37.5 nM. Thus, the affinity of clone SP2 is about twelve times higher than clone 1A6. These impressive results explain why clones SP1 and SP2 work well for immunohistochemistry testing without heat pretreatment at the same concentrations used (2 µg/ml) with clone 1D5 and 1A6 with heat pretreatment.

ER and PR Rabbit Monoclonal Antibody Advantages

The novel rabbit antibody generated by the above-described procedure, clone SP1 recognizing ER has been characterized. The rabbit antibody is specific and sensitive but does not require heat pretreatment in immunohistochemistry on formalin-fixed, paraffin-embedded (FFPE) tissue. Furthermore, the rabbit antibody has appropriate tissue reactivity, giving nuclear staining in epithelial cell tissues known ER status. It also shows reactivity with a predicted band on Western blotting. ELISA results show that the novel rabbit monoclonal antibody clone SP1 has a higher affinity (over eight times the difference) than the previously used mouse monoclonal antibody (clone 1D5).

In general, immunohistochemistry is considered a simple, reliable and economical method for determination of ER status. Immunohistochemistry also has some inherited advantages compare to biochemistry methods. For example, immunohistochemistry can be applied on archive tissue sections. Immunohistochemistry can also work on small samples, especially in situ diseases.

Several groups showed that the existing mouse antibody clone 1D5 is the current best antibody in immunohistochemistry for determination of ER status. Immunohistochemistry testing with mouse antibody ER clone 1D5 in paraffin sections provided the highest correlation with endocrine response. ER can be detected in routine tissue sections processed with target retrieval (heat pretreatment) and mouse antibody ER clone 1D5 can be relied upon to provide accurate prognostic information regarding response to endocrine therapies in breast cancer. At present, mouse antibody ER clone 1D5 is the most commonly used antibody of several commercial available antibodies to ER.

However, the novel rabbit monoclonal antibody of the present invention provides even better results. Most significantly, the novel rabbit monoclonal antibody of the present invention allows immunohistochemistry testing to be performed without heat pretreatment. This significantly simplifies the tissue sample preparation. Furthermore, this will allow the immunohistochemistry testing preparation to easily be automated. Even though the epitopes for clone SP1 and 1D5 are different (clone SP1 recognizes c-terminus of human ER alpha, while clone 1D5 recognizes A/B region, the N-terminal part of human ER alpha), comparative study showed that the new rabbit monoclonal antibody SP1 had almost same results as the mouse antibody ER1D5 except in three cases. In those three cases, the results were strong with SP1 but weak with 1D5, however, they were rated positive with either of the antibodies used. Furthermore, with the new rabbit monoclonal antibody SP1, twenty-one cases were negative, which were exactly the same cases that were negative with mouse antibody 1D5. These results suggested that the new rabbit monoclonal antibody SP1 is more sensitive than mouse antibody 1D5 and has same specificity as 1D5 in immunohistochemistry testing.

Epitopes for clones SP2 and 1A6 are not clear. However, according to ELISA affinity assay, the epitopes of both the clones are located within 412-562 aa of human PR B Form.

With the mouse antibody 1D5, target retrieval is performed to expose the masked antigen to produce stronger staining in immunohistochemistry. Target retrieval such as heat pretreatment is a necessary step to achieve satisfactory results for the currently available ER/PR antibodies used in immunohistochemistry on formalin-fixed, paraffin-embedded tissue. Heat pretreatment by microwave heating of tissue sections in citrate buffer is a widely used method for target retrieval but often results in loss of tissue sections. And target retrieval is also a time consuming step that may produce some other problems. For example, target retrieval may cause increased staining of the background and inconsistency of the results. Thus, by eliminating the need of pretreatment, the new antibodies of the present invention provide a prominent advancement in immunohistochemistry assessment of ER status. The antibodies of the present invention allow the assessment of ER status become simpler, quicker and its results will be more comparable in different lab. Thus, with the antibody of the present invention, it will be easier to standardize the immunohistochemistry methods for assessment of ER status.

In addition to immunohistochemistry testing, these antibodies could be used for many other applications. For example, the new antibodies could also be used for western blotting (for the ER antibody), immunoprecipitation, gel supershift, ligand blocking (neutralization), and affinity purification. The new lagomorph derived antibodies should be better than the existing mouse monoclonal antibodies because of their higher affinity. The new lagomorph derived antibodies are definitely better than mouse monoclonal antibodies when used on mouse tissues because of cross reaction that anti-mouse antibodies have.

Rabbit Monoclonal Antibody Humanization

Besides their use in immunohistochemistry and other testing, the lagomorph derived antibodies may have therapeutic properties. Although there may be therapeutic properties of the antibodies for in humans, there may be problems associated with using the lagomorph derived antibodies within a human. For example, because the lagomorph antibodies originate in a different species, the lagomorph antibodies may be immunogenic within humans. Thus, the human body may produce a neutralizing antibody response. The human's neutralizing antibody response will likely hamper any therapeutic benefit from the lagomorph antibody, especially for long term treatments such as long-term cancer treatments. To overcome these problems, the lagomorph antibody may be "humanized."

Humanizing an antibody consists of transplanting the combining-site of the nonhuman antibody onto a human antibody. This may be performed by grafting the nonhuman complementary determining regions (CDRs) onto human framework and constant regions or by transplanting the entire nonhuman variable domains but hiding them with a human-like surface by replacement of certain exposed residues. Details on creating a humanized antibody are disclosed in U.S. Pat. No. 5,472,693 entitled "High affinity humanized anti-CEA monoclonal antibodies" which is hereby incorporated by reference.

In a preferred embodiment of the present invention, the complementary determining regions (CDRs) from the rabbit monoclonal antibody are transferred to a human antibody framework. Specifically, the CDRs of the rabbit monoclonal antibody are transferred to a human IgG2 heavy chain and to a human kappal light chain. Six (heavy chain) and two (light chain) amino acids are transferred from framework regions. This generates a humanized monoclonal antibody that retained the specificity of the rabbit parent antibody. The humanized monoclonal antibody may then be used for therapeutic purposes but will be less immunogenic than the original rabbit antibody.

The foregoing has described ER and PR monoclonal antibodies and a method for creating such monoclonal antibodies. It is contemplated that changes and modifications may be made by one of ordinary skill in the art, to the materials and arrangements of elements of the present invention without departing from the scope of the invention.

We claim:

1. A rabbit monoclonal antibody having a specific affinity for human progesterone receptor that is higher than that of murine monoclonal antibody 1 A6, wherein the rabbit monoclonal antibody specifically binds an epitope within amino acids 412-562 of the progesterone receptor B form present in a fresh tissue section and present, in the absence of a tissue section processing step involving proteolytic digestion or heat treatment for antigen retrieval, in a formalin-fixed, paraffin-embedded tissue section after processing steps of deparaffinization and rehydration.

2. The antibody of claim 1, wherein the specific affinity for the progesterone receptor is about twelve times higher than that of the murine monoclonal antibody 1A6.

3. A method for performing immunohistochemistry for the human progesterone receptor on a formalin-fixed, paraffin-embedded tissue section after processing steps of deparaffinization and rehydration in the absence of a tissue section processing step involving proteolytic digestion or heat treatment for antigen retrieval, comprising the step of contacting the tissue section with the antibody of claim 1 to specifically detect the progesterone receptor.

4. A method for performing immunohistochemistry for the human progesterone receptor on a formalin-fixed, paraffin-embedded tissue section after processing steps of deparaffinization and rehydration in the absence of a tissue section processing step involving proteolytic digestion or heat treatment for antigen retrieval, comprising the step of contacting the tissue section with the antibody of claim 2 to specifically detect the progesterone receptor.

5. A method for selecting a monoclonal antibody for immunohistochemistry analysis of a human progesterone receptor, said method comprising the steps of:
   a) contacting a rabbit monoclonal antibody of a plurality of rabbit monoclonal antibodies with a formalin-fixed, paraffin-embedded tissue section that contains the progesterone receptor, in the absence of a tissue section processing step involving proteolytic digestion or heat treatment for antigen retrieval, and after processing steps of deparaffinization and rehydration; and
   b) detecting specific binding of the monoclonal antibody to the progesterone receptor in the absence of antigen retrieval to select the monoclonal antibody from the plurality of monoclonal antibodies for immunohistochemistry analysis of the progesterone receptor.

6. The method of claim 5, Further comprising prior to the contacting step, the step of performing an ELISA with supernalants from hybridomas to identify the recited plurality of rabbit monoclonal antibodies.

7. The method of claim 5, further comprising after the selecting step, the step of humanizing the rabbit monoclonal antibody.

8. The method of claim 5, wherein the rabbit monoclonal antibody specifically binds an epitope within amino acids 412-562 of the progesterone receptor alpha protein present in the formalin-fixed, paraffin-embedded tissue section without antigen retrieval.

9. The method of claim 5, wherein the rabbit monoclonal antibody specifically binds an epitope within amino acids 412-562 of the progesterone receptor B form present in the formalin-fixed, paraffin-embedded tissue section without antigen retrieval, and the specific affinity for the progesterone receptor is about twelve times higher than that of murine monoclonal antibody 1A6.

* * * * *